United States Patent [19]
Yamauchi et al.

[11] Patent Number: 5,586,732
[45] Date of Patent: Dec. 24, 1996

[54] CRUSHING AND DISPERSING BAG

[75] Inventors: Hiroshige Yamauchi, Kobe; Shonosuke Nishi, Kawanishi, both of Japan

[73] Assignee: Shimakyu Chemical Co., Ltd., Osaka, Japan

[21] Appl. No.: 360,746

[22] PCT Filed: Jul. 12, 1993

[86] PCT No.: PCT/JP93/00963

§ 371 Date: Dec. 23, 1994

§ 102(e) Date: Dec. 23, 1994

[87] PCT Pub. No.: WO95/02457

PCT Pub. Date: Jan. 26, 1995

[30] Foreign Application Priority Data

Jan. 16, 1992 [JP] Japan ........................... 4-5808

[51] Int. Cl.$^6$ ........................................ A47J 43/04
[52] U.S. Cl. ..................... 241/168; 241/102; 241/199; 383/117
[58] Field of Search ................. 241/102, 168, 241/199, 201; 383/116, 117, 119

[56] References Cited

U.S. PATENT DOCUMENTS

| | | | |
|---|---|---|---|
| 2,413,151 | 12/1946 | Dell | 241/168 |
| 2,664,675 | 1/1954 | Monica | 241/102 X |
| 3,550,839 | 12/1970 | Clayton et al. | 383/116 |
| 4,196,534 | 4/1980 | Shibamoto | 383/117 X |
| 4,285,998 | 8/1981 | Thibodeau | 383/116 X |

FOREIGN PATENT DOCUMENTS

| | | | |
|---|---|---|---|
| 99369 | 6/1983 | Japan | 383/117 |
| 64-41300 | 3/1989 | Japan . | |
| 45359 | 2/1990 | Japan | 383/117 |

Primary Examiner—Timothy V. Eley
Attorney, Agent, or Firm—Davis, Bujold & Streck, P.A.

[57] ABSTRACT

The invention was developed in order to effectively crush and disperse various samples easily and efficiently without using any expensive device. By laminating a polyethylene film 3, a net member 7, a net member 9 and a polyethylene film 5 in sequence and welding these members to one another at weld portions 13a and 13b, a bag member 15 is formed. Further by forming a fastener 17 in the vicinity of an opening 15a, a crushing and dispersing bag 1 is completed. After a sample and a dispersing medium are introduced through the opening 15a, the bag is sealed with the fastener 17. Subsequently, when the crushing and dispersing bag 1 is squeezed, the sample is ground by the file-like irregularities formed by the net members 7 and 9 on the inner surface of the bag 1.

19 Claims, 2 Drawing Sheets

CRUSHING AND DISPERSING BAG

TECHNICAL FIELD

This invention relates to a crushing and dispersing bag for mechanically crushing, comminuting and dispersing foodstuffs, soil or other samples.

BACKGROUND ART

Conventionally, a mortar was used for mechanically crushing and dispersing foodstuffs, soil or other samples. In the field of biochemistry, for the sake of microbiological examination or physiological examination, organic cell samples are mechanically crushed and dispersed to emulsify. Thus, the sample cells are so-called homogenized. For such homogenization, a sample and a dispersion medium are introduced into a cup. By rotating a screw inserted in the cup, the sample is crushed and dispersed. Such device is a so-called cup type homogenizer. Alternatively, a polyvinyl bag with the sample and the dispersion medium sealed therein is inserted between a pair of plates, which slide in the direction of a normal line and approach to or depart from each other. Pressure applied by the pair of plates crushes and disperses the sample. By using this (for example the trade name Stomacher generally distributed by Gunze Sangyo Kabushiki Kaisha) or other, the sample is crushed and dispersed efficiently.

However, when the cup type homogenizer is used, the cup needs to be cleaned or sterilized before the sample is introduced into the cup. Therefore, when a number of samples are crushed and dispersed, a number of cups need to be prepared, which is troublesome.

Since a disposable polyvinyl bag is used for Stomacher, a number of samples can be efficiently crushed and dispersed. However, Stomacher is so large that it cannot be transported. Additionally, since just pressure is applied to the bag, Stomacher is inappropriate for crushing and dispersing octopuses, squids or other resilient samples. Further, the cup type homogenizer and Stomacher are both expensive.

Wherefore, the object of the present invention is to easily, efficiently and effectively crush and disperse various samples without using an expensive device.

DISCLOSURE OF THE INVENTION

To attain the aforementioned object, the present invention provides a crushing, comminuting and dispersing bag having:

a synthetic resin bag member provided with file-like unevenness or irregularities on the inner surface thereof, and a sealing member for sealing the opening of said synthetic resin bag member.

In operation of the aforementioned structure of the present invention, the sample to be crushed and the dispersion medium are introduced into the synthetic resin bag member and the opening in the bag member is sealed with the sealing member. Subsequently, by squeezing the bag member, the sample is crushed and comminuted by the file-like irregularities provided on the inner surface of the bag member. The sample can thus be crushed and dispersed in the dispersion medium.

The present invention requires no expensive devices. Just by squeezing the bag member with hands or other means, the sample can be easily crushed, comminuted and dispersed. Further in the present invention, the sample rubs against the irregularities and is thus mechanically ground. Therefore, octopuses, squids or other resilient samples can be effectively crushed, comminuted and dispersed.

Additionally, the present invention has a simple structure and is inexpensively manufactured of synthetic resin or other material. Further, the bag according to the present invention can be easily transported and stored. With a number of disposable bags, a number of samples can be efficiently crushed and dispersed.

Especially, since the file-like irregularities are provided by laying a net member on the inner surface of the synthetic resin bag member, the bag of the present invention can be easily manufactured just by adding the net member laminating step to the manufacturing process of the synthetic resin bag provided with a sealing member.

BEST MODE FOR CARRYING OUT THE INVENTION

Figure 1:
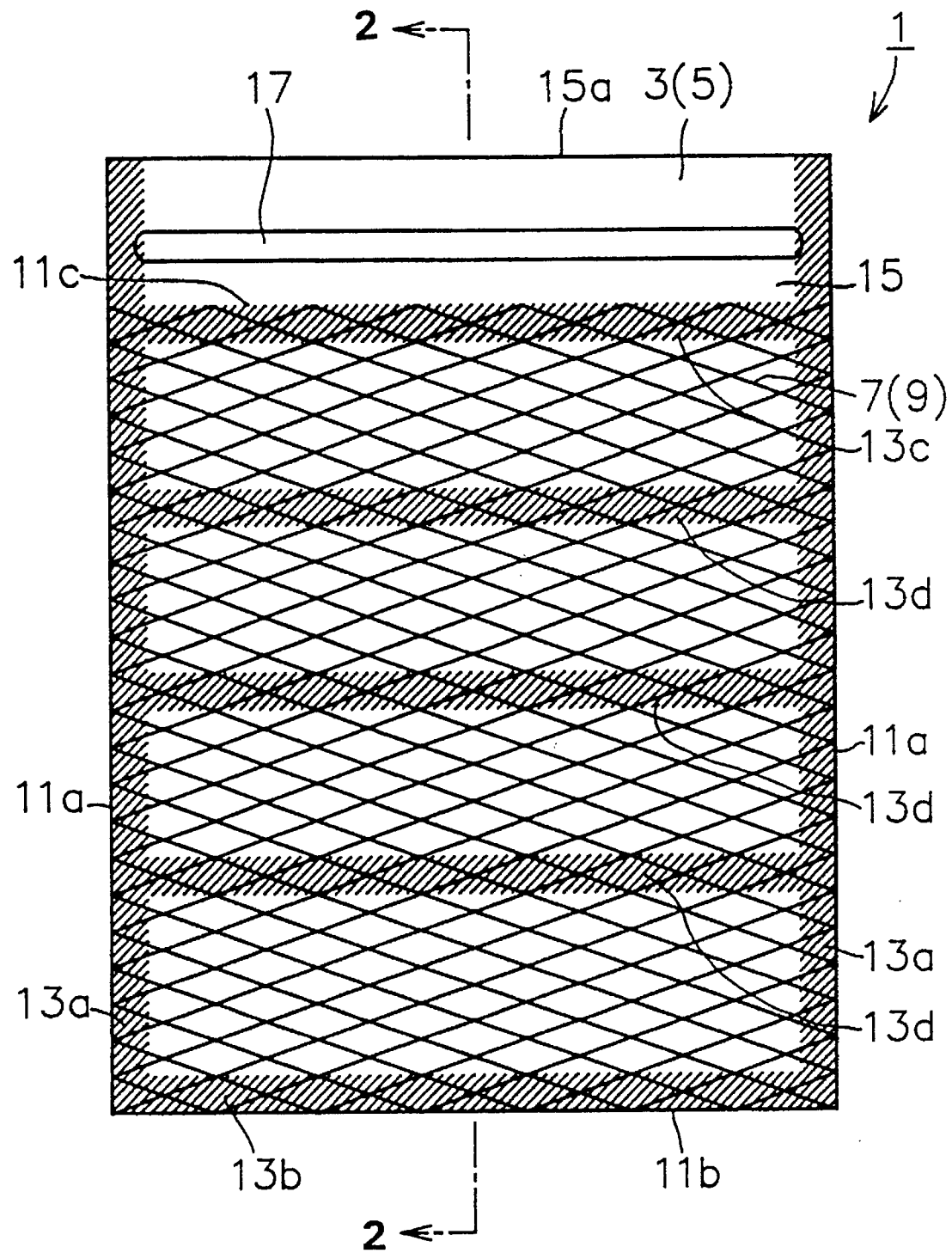
FIG. 1 is a plan view showing the structure of a crushing and dispersing bag embodying the invention.

The embodiment of the present invention is now explained by referring to the drawings: FIG. 1 is a plan view showing a structure of a crushing and dispersing bag 1 of the embodiment; and FIG. 2 is the cross-sectional view taken along line 2—2 of FIG. 1.

As shown in FIG. 1, the crushing and dispersing bag 1 is composed of a pair of rectangular and transparent polyethylene films 3,5 and a pair of polyethylene resin net members 7,9 having the same width as that of the polyethylene films 3,5. The length of the net members 7,9 is slightly shorter than that of the films 3,5. The polyethylene films 3,5 and the net members 7,9 are laid with both side edges 11a and a bottom edge 11b aligned with the counterpart edges. The polyethylene film 3, the net member 7, the net member 9 and the polyethylene film 5 are laminated in sequence, such that the net members 7 and 9 form two intersecting pluralities of parallel ridges, such as ridges on a file. These members are welded to one another at weld portions 13a and 13b having a specified width and provided on the side edges 11a and the bottom edge 11b. Thus, the polyethylene films 3 and 5 form a bag member 15 having an opening 15a defined by the edge opposite to the bottom edge 11b.

Figure 2:
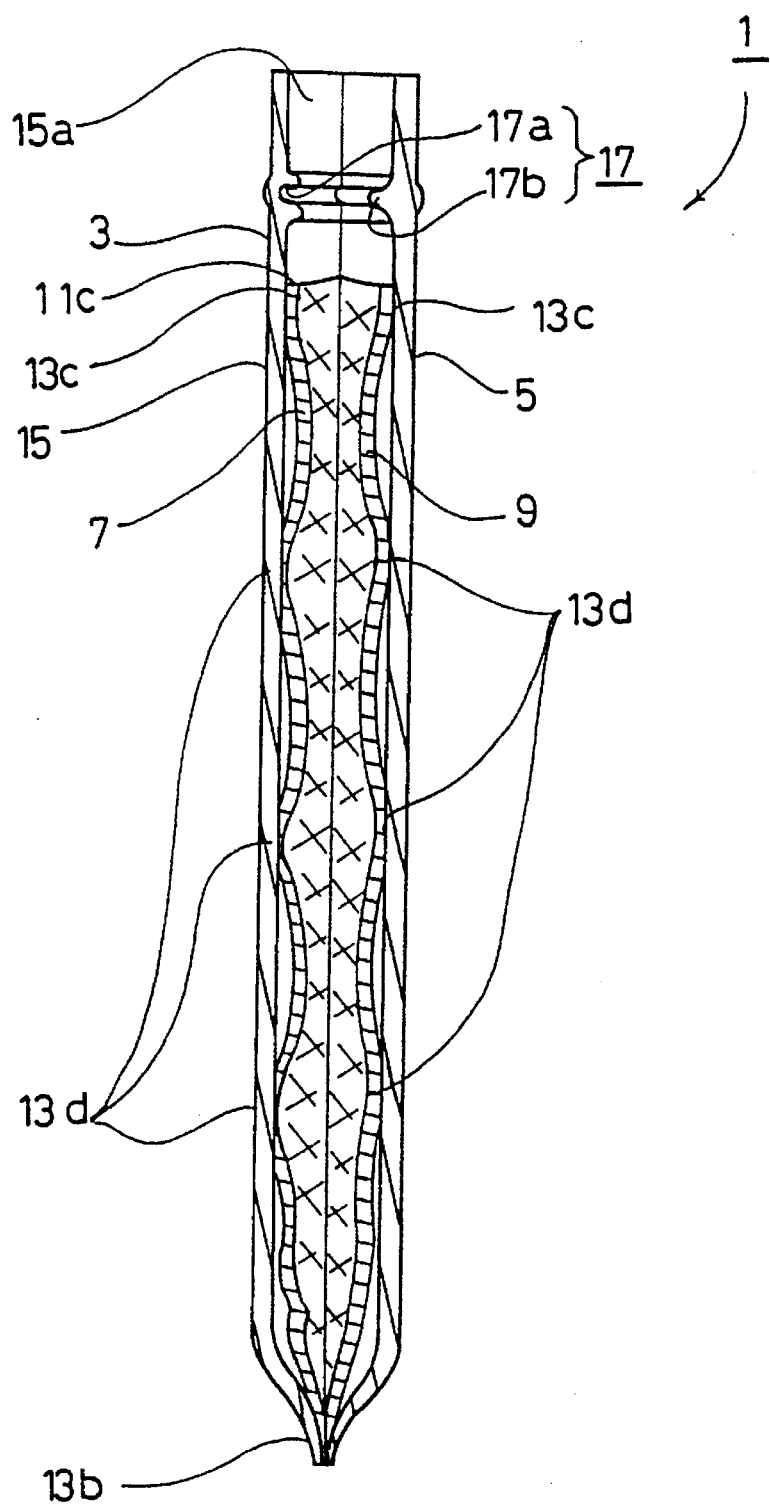
FIG. 2 is a cross-sectional view also showing the structure of the crushing and dispersing bag of the embodiment.

Further as shown in FIG. 2, the polyethylene film 3 and the net member 7 are welded to each other at a weld portion 13c provided on the edge 11c opposite to the edge 11b of the net member 7 and at three parallel weld portions 13d between the edges 11b and 11c. In the same way, the polyethylene film 5 and the net member 9 are welded to each other at the weld portions 13c and 13d.

In the part having no lamination of the net members 7 and 9 on the polyethylene films 3 and 5, adjacent to the opening 15a, a zipper or fastener 17 as a sealing member is provided parallel with the edge 11b. The fastener 17 is composed of a groove 17a extended between the weld portions 13a provided on both sides of the polyethylene film 3, and a ridge 17b extended between the weld portions 13a on both sides of the polyethylene film 5. The ridge 17b opposed to the groove 17a is engaged in the groove 17a, thereby forming a known sealing member.

The size of the bag member is not especially limited. When 5 g to 10 g of the sample is used and the dispersion medium has the amount ten times as large as that of the sample, the bag preferably has a width of 6 cm to 15 cm and a length of 10 cm to 25 cm, so that the bag can be squeezed with hands and fingers to crush, comminute and disperse samples. Additionally, the thickness of the synthetic resin film composing the bag member is not limited and varies with the material of the film. The film can have any thickness, so long as the bag is soft and resilient enough to be squeezed by hand and sufficiently strong to resist tearing. The preferable thickness of a polyethylene film, for example, is about 0.04 mm to 0.12 mm.

Although thread diameter and mesh size of the net members are not especially limited, the thread diameter between 0.2 mm and 0.8 mm and the mesh size between 2 mm and 8 mm are preferable for the efficient crushing and dispersing. Further, the material of the net members is not especially limited. Polyethylene, polypropylene or any other material is, however, preferable because the material does not dissolve in the dispersion medium and has a sufficient strength.

In operation of the crushing and dispersing bag 1 having the aforementioned structure, the sample to be crushed, comminuted and the dispersion medium are introduced from the opening 15a into the bag 1, and the opening 15a is sealed with the fastener 17 for use. Subsequently, when the crushing and dispersing bag 1 is squeezed, the sample rubs against the file-like irregularities formed by the net members 7,9 on the inner surface of the polyethylene films 3,5, respectively, and is thus crushed, comminuted and dispersed.

The applicants of the present invention conducted the experiment of the so-called homogenizer by using the crushing and dispersing bag 1. The bag 1 was composed of the net members 7,9 having a thread diameter of 0.4 mm and a mesh size of 2 mm and the polyethylene films 3,5 having a thickness of 0.08 mm. In the experiment organic cell samples were crushed, comminuted and dispersed to emulsify as follows.

First, the crushing and dispersing bag 1 was sterilized with ethylene oxide gas. After each of the samples given in Table 1 was cut into pieces, 2.0 g each of the samples was introduced into each of a number of the crushing and dispersing bags 1. Subsequently, after 18.0 ml of physiological salt solution was each injected to the crushing and dispersing bag 1, the bag 1 was sealed with the fastener 17. The crushing and dispersing bag 1 can be sterilized by the irradiation of gamma ray.

As aforementioned, the crushing and dispersing bag 1 was prepared for each of the samples. The bag containing a soft sample was manually squeezed for one to two minutes; and the one containing a hard sample for two to three minutes. The samples were thus comminuted homogenized. While the crushing and dispersing bag 1 was manually squeezed, the degree of comminution of the sample was visually examined and the portion having a low degree of comminution was mainly squeezed.

For reference examples, the same samples as those used in the embodiment were homogenized as follows.

Reference Example 1: 10.0 g of sample was introduced into a sterilized homogenizer cup. After 90.0 ml of sterilized physiological salt solution was injected into the cup, the cup screw was rotated at 10000 rpm so as to homogenize the sample for about one minute. Homogenizer AM-12 (the trade name manufactured by Kabushiki Kaisha Nihon Seiki Seisakusho) was used as the cup type homogenizer.

Reference Example 2: 10.0 g of sample was introduced into a sterilized polyvinyl bag for Stomacher. After 90.0 ml of sterilized physiological salt solution was injected into the bag and the bag was sealed, the sample was homogenized for one minute. Stomacher 400 (the tradename generally distributed by Gunze Sangyo Kabushiki Kaisha) was used.

The samples homogenized in respective ways were examined for bacteria. The extracting efficiency of gained bacteria is shown in Table 1 on the next page.

TABLE 1

| KIND OF SAMPLES | EMBODIMENT | REFERENCE EXAMPLE 1 | REFERENCE EXAMPLE 2 |
|---|---|---|---|
| PRAWN | 26500 | 25500 | 25000 |
|  | (103.9) | (100.0) | (98.0) |
| RAW SQUID | 51500 | 48000 | 45500 |
|  | (107.3) | (100.0) | (94.8) |
| BOILED OCTOPUS | 750 | 780 | 600 |
|  | (96.2) | (100.0) | (76.9) |
| PICKLED RADISH | 12150 | 12200 | 260 |
|  | (99.6) | (100.0) | (21.3) |
| BROILED EEL | 2380 | 2300 | 2790 |
|  | (103.5) | (100.0) | (111.6) |

THE UPPER NUMERICAL VALUE: THE NUMBER OF GENERAL BACTERIA PER 1 g OF SAMPLE
THE LOWER NUMERICAL VALUE WITHIN THE PARENTHESIS: EXTRACTING EFFICIENCY, WHEN THE EFFICIENCY OF THE HOMOGENIZING METHOD OF REFERENCE EXAMPLE 1 IS SET AS 100%

As shown in Table 1, in the embodiment, the extracting efficiency almost the same as that of the homogenizing method according to the reference example 1 can be obtained. Therefore, in the embodiment any sample can be homogenized sufficiently. Especially regarding prawns and raw squids, the embodiment shows the extracting efficiency superior to that of any reference example. Since the sample rubs against the net members 7 and 9 and is ground in the embodiment, even the resilient material can be effectively crushed, comminuted and dispersed.

As aforementioned, the crushing and dispersing bag 1 of the embodiment requires no expensive devices. By squeezing the crushing and dispersing bag 1 by hand, the sample can be easily crushed, comminuted and dispersed. Since in the crushing and dispersing bag 1 the sample is ground in contact with the net members 7 and 9, various samples can be effectively crushed and dispersed. Furthermore, the crushing and dispersing bag 1 has such a simple structure that it can be inexpensively manufactured of polyethylene resin. The bag 1 can be easily manufactured just by adding the step of laminating the net members 7 and 9 to the manufacturing process of a polyvinyl bag provided with a fastener. The invention can provide a very inexpensive crushing and dispersing bag 1.

The crushing and dispersing bag 1 of the embodiment can be easily transported and stored. With a number of disposable bags, a corresponding number of samples can be efficiently crushed and dispersed. Since the bag is formed of transparent polyethylene films 3,5, the degree of crush of the sample contained in the sealed bag can be visually inspected. Therefore, by mainly squeezing the portions of the sample having a low degree of comminution, the sample can be uniformly crushed and dispersed.

In the aforementioned embodiment, foodstuffs and other organic cell samples were crushed and dispersed. The crushing and dispersing bag 1, however, can be used for crushing and dispersing soil or other various substances. In the embodiment the net members 7 and 9 form the file-like irregularities, i.e. parallel ridges or grooves, on the inner surface of the films 3 and 5, respectively. However, the irregularities can be formed directly on the inner surface of the polyethylene films 3 and 5. Furthermore, in the embodiment the fastener 17 as the sealing member is formed integrally with the polyethylene films 3 and 5. The sealing member can be formed separately from the bag member 15. For example, the bag can be sealed with a clip attached to the vicinity of the opening 15a.

INDUSTRIAL APPLICABILITY

As detailed above, the crushing and dispersing bag of the present invention requires no expensive devices. By squeezing the bag member with hands or other means, the sample can be easily crushed, comminuted and dispersed. Also in the present invention, the sample is ground by the irregularities of the inner surface of the bag. Therefore, various samples can be effectively crushed, comminuted and dispersed. Furthermore, the bag of the present invention can be easily and inexpensively manufactured of synthetic resin and other material. The bag can be easily transported and stored as well. With a number of disposable bags, many samples can be efficiently crushed, comminuted and dispersed.

Especially, when the file-like irregularities, ridges are provided on the inner surface of the synthetic resin bag member by the laminating step, the bag can be easily manufactured. Specifically, the step of laminating the net members is just added to the manufacturing process of the synthetic resin bag with the sealing member attached thereto.

We claim:

1. A crushing and dispersing bag comprising:

a synthetic resin bag member open at one end thereof and being provided with at least a first plurality of parallel ridges, sized to facilitate comminution of material inserted into the synthetic resin bag member by grinding the material into smaller pieces, on an inner surface of the synthetic resin bag member; and a sealing member for sealing the open end of the synthetic resin bag member;

wherein said synthetic resin bag member has two opposed inner surfaces and said sealing member comprises a groove provided on one of the inner surfaces and a projection provided on the other of the inner surfaces, which projection is sized to be received in the groove in an interference fit, to thereby seal the bag member.

2. A crushing and dispersing bag according to claim 1, wherein the first plurality of parallel ridges are integrally formed on an inner surface of the synthetic resin bag member.

3. A crushing and dispersing bag according to claim 2, wherein a second plurality of parallel ridges, that are at an angle to and intersect with the first plurality of ridges, are integrally formed on an inner surface of the synthetic resin bag member.

4. A crushing and dispersing bag according to claim 3, wherein the synthetic resin bag member has two inner surfaces and each said inner surface has said first and second plurality of parallel ridges integrally formed thereon.

5. A crushing and dispersing bag according to claim 3, wherein the bag member is formed of synthetic resin film with a thickness from about 0.04 mm to about 0.12 mm and the ridges have a width and height from about 0.2 mm to about 0.8 mm.

6. A crushing and dispersing bag according to claim 5, wherein the ridges are spaced to have a mesh size from about 2 mm to about 8 mm.

7. A crushing and dispersing bag according to claim 6, wherein the film has a thickness of about 0.08 mm, and the ridges have a width and height of about 0.4 mm and are spaced to have a mesh size of 2 mm.

8. A crushing and dispersing bag according to claim 1, wherein the groove is formed in the one inner surface and the projection is a ridge integrally formed on the other inner surface.

9. A crushing and dispersing bag comprising:

a synthetic resin bag member open at one end thereof and being provided with a first plurality of parallel ridges and a second plurality of parallel ridges, that are at an angle to and intersect the first plurality of parallel ridges, on an inner surface of the synthetic resin bag member; and a sealing member for sealing the open end of the synthetic resin bag member;

wherein the ridges are provided by a net member laminated on the inner surface of the synthetic resin bag member and the ridges are sized to facilitate comminution of material inserted into the synthetic resin bag member by grinding the material into smaller pieces.

10. A crushing and dispersing bag according to claim 9, wherein the synthetic resin bag member is formed of a synthetic resin film and the net member is formed of synthetic resin fiber.

11. A crushing and dispersing bag according to claim 10, wherein the synthetic resin film is from about 0.04 mm to about 0.12 mm thick and the synthetic resin fiber has a diameter from about 0.2 mm to about 0.8 mm.

12. A crushing and dispersing bag according to claim 11, wherein the synthetic resin fiber is interwoven to form a net having a mesh size from about 2 mm to about 8 mm.

13. A crushing and dispersing bag according to claim 12, wherein the film has a thickness of 0.08 mm, the synthetic resin fiber has a diameter of 0.04 mm and is interwoven to form a net having a mesh size of 2 mm.

14. A crushing and dispersing bag according to claim 10, wherein the synthetic resin film and the synthetic resin fiber are formed of one of polyethylene and polypropylene.

15. A crushing and dispersing bag according to claim 9, wherein the bag member has two opposed inner surfaces and there are two said net members, each said net member is laminated to a corresponding said inner surface of the bag.

16. A crushing and dispersing bag according to claim 15, wherein each said net member is welded at predetermined intervals to the corresponding inner surface of the bag member.

17. A crushing and dispersing bag according to claim 16, wherein said sealing member comprises a groove provided on one of the inner surfaces and a projection provided on the other of the inner surfaces, which projection is sized to be received in the groove in an interference fit, to thereby seal the bag member.

18. A crushing and dispersing bag according to claim 16, wherein said sealing member comprises a clamp provided separately from the bag member and attached to an outer surface of the bag member.

19. A crushing dispersing bag according to claim 9, wherein said sealing member comprises a clamp provided separately from the bag member and attached to an outer surface of the bag member.

\* \* \* \* \*